(12) United States Patent
Zetina-Rocha et al.

(10) Patent No.: US 7,939,662 B2
(45) Date of Patent: May 10, 2011

(54) AMORPHOUS ZIPRASIDONE HYDROCHLORIDE (5-[2-[4-(1,2-BENZISOTHIAZOL-3-YL)-1-PIPERAZINYL]ETHYL]-6-CHLORO-1,3-DIHYDRO-2H-INDOL-2-ONE HYDROCHLORIDE) AND PROCESSES TO PRODUCE THE SAME

(75) Inventors: Carlos Zetina-Rocha, Brantford (CA); Allan W. Rey, Brantford (CA); Matthew A. Buck, Waterloo (CA); Lotfi Derdour, Brantford (CA); Stephen E. Horne, Burlington (CA); Keshava K. S. Murthy, Ancaster (CN)

(73) Assignee: Apotex Pharmachem Inc., Branford (CA)

( * ) Notice: Subject to any disclaimer, the term of this patent is extended or adjusted under 35 U.S.C. 154(b) by 606 days.

(21) Appl. No.: 11/987,926

(22) Filed: Dec. 6, 2007

(65) Prior Publication Data

US 2009/0030204 A1    Jan. 29, 2009

Related U.S. Application Data

(62) Division of application No. 10/884,991, filed on Jul. 7, 2004, now abandoned.

(30) Foreign Application Priority Data

May 14, 2004   (CA) ...................................... 2467538

(51) Int. Cl.
 *C07D 417/00*   (2006.01)
(52) U.S. Cl. ...................................... 544/368
(58) Field of Classification Search .................. 544/368; 514/254.04
 See application file for complete search history.

(56) References Cited

U.S. PATENT DOCUMENTS

| 4,831,031 | A | 5/1989 | Lowe, III et al. |
| 5,206,366 | A | 4/1993 | Bowles |
| 5,312,925 | A | 5/1994 | Allen et al. |
| 5,338,846 | A | 8/1994 | Busch et al. |
| 5,935,960 | A | 8/1999 | Walinsky et al. |
| 6,150,366 | A | 11/2000 | Arenson et al. |
| 7,087,611 | B2 | 8/2006 | Zetina-Rocha et al. |
| 2004/0152711 | A1 | 8/2004 | Reddy et al. |

FOREIGN PATENT DOCUMENTS

| CA | 2166203 | 1/1995 |
| CA | 2245269 | 1/2003 |
| CA | 2252898 | 4/2003 |
| CA | 2471219 | 12/2005 |
| EP | 0901786 | 3/1999 |
| WO | WO 9500510 | 1/1995 |
| WO | WO 0059489 | 10/2000 |
| WO | WO 03/070246 | 8/2003 |
| WO | WO 2004/050655 | 6/2004 |
| WO | WO 2005/035531 | 4/2005 |

OTHER PUBLICATIONS

McMurry, J., Organic Chemistry, 1988, Brooks/Cole Publishing Company, p. 355.
Merck Index, 12 edition, 1996, p. 1044.
Smith, M.B., Orgainc Synthesis, 1994, McGraw-Hill, Inc. p. 125.

*Primary Examiner* — Paul V. Ward

(57) ABSTRACT

The present invention relates to a new and useful amorphous form of ziprasidone hydrochloride (5-[2-[4-(1,2-benzisothiazol-3-yl)-1-piperazinyl]ethyl]-6-chloro-1,3-dihydro-2H-indol-2-one hydrochloride) and preparations thereof.

34 Claims, 3 Drawing Sheets

US 7,939,662 B2

AMORPHOUS ZIPRASIDONE HYDROCHLORIDE (5-[2-[4-(1,2-BENZISOTHIAZOL-3-YL)-1-PIPERAZINYL] ETHYL]-6-CHLORO-1,3-DIHYDRO-2H-INDOL-2-ONE HYDROCHLORIDE) AND PROCESSES TO PRODUCE THE SAME

CROSS REFERENCE TO RELATED APPLICATIONS

This is a divisional application of U.S. patent application Ser. No. 10/884,991, filed on Jul. 7, 2004.

TITLE OF THE INVENTION

New amorphous ziprasidone hydrochloride (5-[2-[4-(1,2-benzisothiazol-3-yl)-1-piperazinyl]ethyl]-6-chloro-1,3-dihydro-2H-indol-2-one hydrochloride) and processes to Produce the same.

BACKGROUND OF THE INVENTION

Ziprasidone hydrochloride (5-[2-[4-(1,2-benzisothiazol-3-yl)-1-piperazinyl]ethyl]-6-chloro-1,3-dihydro-2H-indol-2-one hydrochloride) is a potent neuroleptic agent useful in the treatment of various disorders including schizophrenia, anxiety and pain. It is currently marketed under the proprietary name of Geodon. Ziprasidone hydrochloride is known to exist in three crystalline forms; namely, the monohydrate, hemihydrate and anhydrous form as disclosed in U.S. Pat. Nos. 4,831,031 and 5,312,925, both of which are herein incorporated by reference. U.S. Pat. No. 5,312,925 states that ziprasidone hydrochloride monohydrate is hygroscopically stable, thus alleviating potential problems due to weight changes of the active pharmaceutical ingredient during the final formulation process. Nevertheless a very low aqueous solubility is observed for this crystalline form.

Canadian patent 2,252,898 attempts to overcome some of the deficiencies of the prior art, especially the poor aqueous solubility of ziprasidone hydrochloride monohydrate, by formation of various mesylate hydrate salts.

In U.S. Pat. No. 6,150,366 the poor aqueous solubility is purportedly increased by controlling, by various methods, the mean particle size of the crystalline ziprasidone free base or ziprasidone hydrochloride to a mean particle size equal to or less than about 85 μm.

U.S. Pat. No. 5,935,960 describes another attempt to overcome the poor aqueous solubility of ziprasidone hydrochloride by formation of a pro-drug of ziprasidone, specifically 1-[2-(6-chloro-2,3-dihydro-2-oxo-1H-indol-5-yl)ethyl]-4-[imino(2-mercaptophenyl)methyl]piperazine or one of its pharmaceutically acceptable salts, for instance the dihydrochloride.

Canadian patent 2,245,269 describes numerous compositions comprising of solid spray dried dispersions of sparingly water soluble drugs, including ziprasidone free base, and hydroxypropylmethylcellulose acetate succinate. Again, the form obtained purportedly provides increased aqueous solubility and/or bioavailability.

Therefore, a method which produces an improved form of ziprasidone hydrochloride in high yields and purity, and helps to overcome some of the deficiencies of the known forms is desired.

SUMMARY OF THE INVENTION

It is an object of the present invention to provide a method for the preparation of an improved form of ziprasidone hydrochloride in high yields and purity.

We have surprisingly found that using low-polarity organic solvents such as $C_5$ to $C_{12}$ substituted or unsubstituted cyclic and acyclic hydrocarbons such as hexanes, heptanes, or cyclohexanes; or $C_1$ to $C_3$ chlorinated hydrocarbons such as dichloromethane or chloroform and mixtures thereof to carry out the reaction between ziprasidone free base and anhydrous hydrogen chloride, unexpectedly a novel amorphous form of ziprasidone hydrochloride is obtained. (See FIGS. 1, 2 and 3 to this specification)

Thus, in accordance to an aspect of the present invention there is provided a process for preparing the novel amorphous form of ziprasidone hydrochloride comprising the steps of:
(i) suspending ziprasidone free base in about 5 to 100 volumes of such low-polarity organic solvent or mixture of solvents at a temperature of from about −10 to about 40° C.,
(ii) one of the following steps:
  a) bubbling hydrogen chloride gas for a period between 1 and 12 hours or,
  b) exposing the mixture to a suitable pressure of hydrogen chloride or,
  c) adding a solution of hydrogen chloride in a suitable organic solvent,
(iii) stirring the mixture at a temperature between about −10 and 40° C. until product is produced,
(iv) filtering and washing the solid at ambient temperature,
(v) if required, stirring the solid with a suitable organic solvent between about −10 and 60° C.,
(vi) if required, filtering and washing the solid,
(vii) drying the solid.

Thus according to another aspect of the invention, there is provided a process for producing the novel amorphous form of ziprasidone hydrochloride comprising the steps of:
(i) suspending ziprasidone free base preferably in about 5 to 100 volumes of a low-polarity organic solvent or mixture of solvents at a temperature of from about −10 to about 40° C.,
(ii) adding hydrogen chloride to the suspension,
(iii) recovering the amorphous ziprasidone hydrochloride.

Examples of low polarity organic solvents, which are useful in the reaction of the present invention include, but are not limited to a $C_5$ to $C_{12}$ substituted or unsubstituted cyclic and acyclic hydrocarbon solvent such as hexanes, heptanes, or cyclohexane; or a $C_1$ to $C_3$ chlorinated hydrocarbon solvent such as dichloromethane or chloroform, and their mixtures thereof. The most preferred solvent is heptanes or dichloromethane.

Examples of suitable organic solvents, which are useful for preparing solutions of anhydrous hydrogen chloride [step (iv)], include but are not limited to, isopropanol, ethanol and ethyl ether.

This novel amorphous form has advantageous properties relative to those of the prior art, for instance, better water solubility and potentially improved bioavailability. It also has the advantage of simplicity in that it avoids the necessity of having to resort to specialized preparation methods. For instance this more aqueous soluble amorphous form does not necessitate the use of a different salt form of ziprasidone as taught in Canadian patent 2,252,898 or a pro-drug of ziprasidone as taught in U.S. Pat. No. 5,935,960. Also it avoids the use of specialized spray dried dispersion compositions of ziprasidone free base as taught in Canadian patent 2,245,269 or specialized process equipment to ensure that the mean particle size produced is below 85 μm as taught in U.S. Pat. No. 6,150,366.

DETAILED DESCRIPTION OF THE INVENTION

The following examples illustrate the preparation of ziprasidone hydrochloride anhydrate and amorphous ziprasidone hydrochloride and are not to be construed as limiting the scope of the invention in any manner.

Example 1

Figure 1:
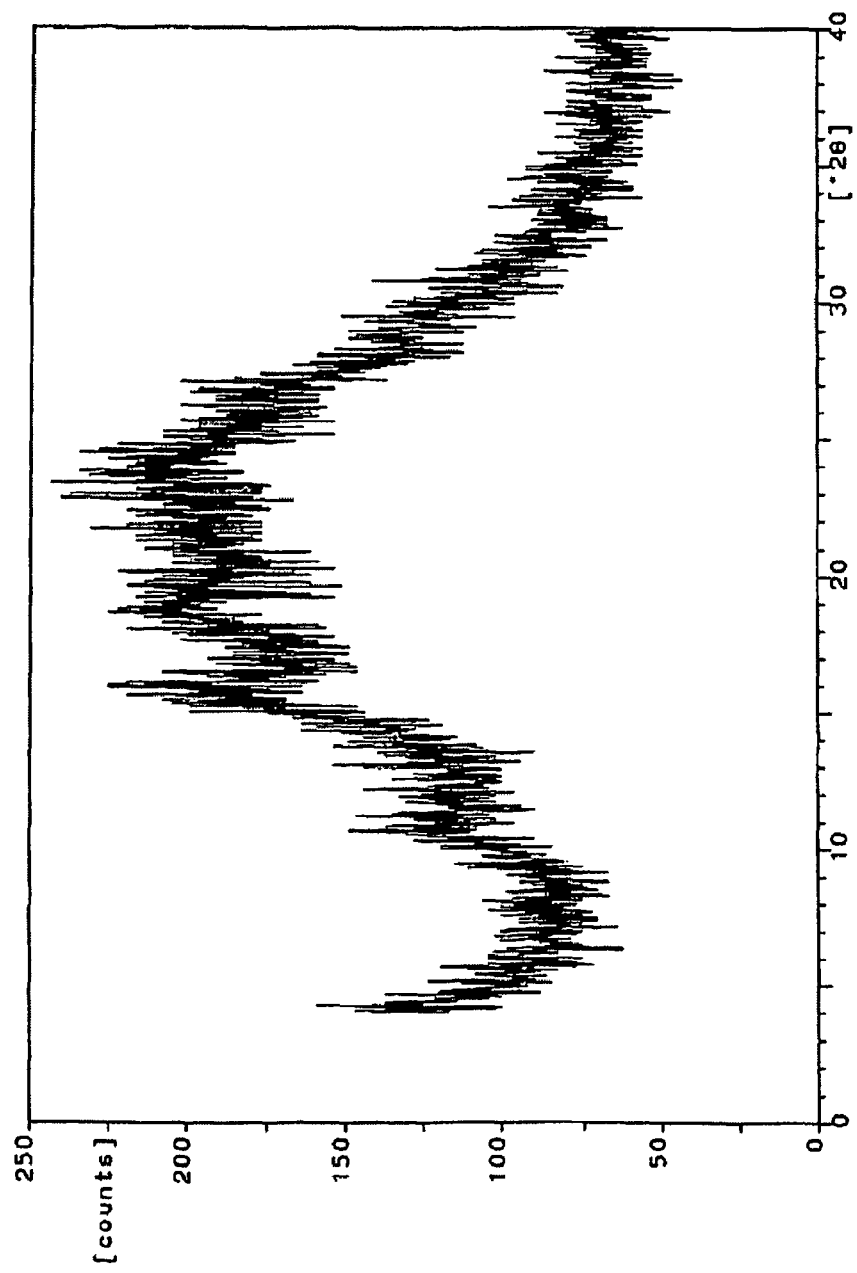
FIG. 1 is a typical example of a PXRD Diffractogram of a sample of Amorphous Ziprasidone Hydrochloride
Figure 2:
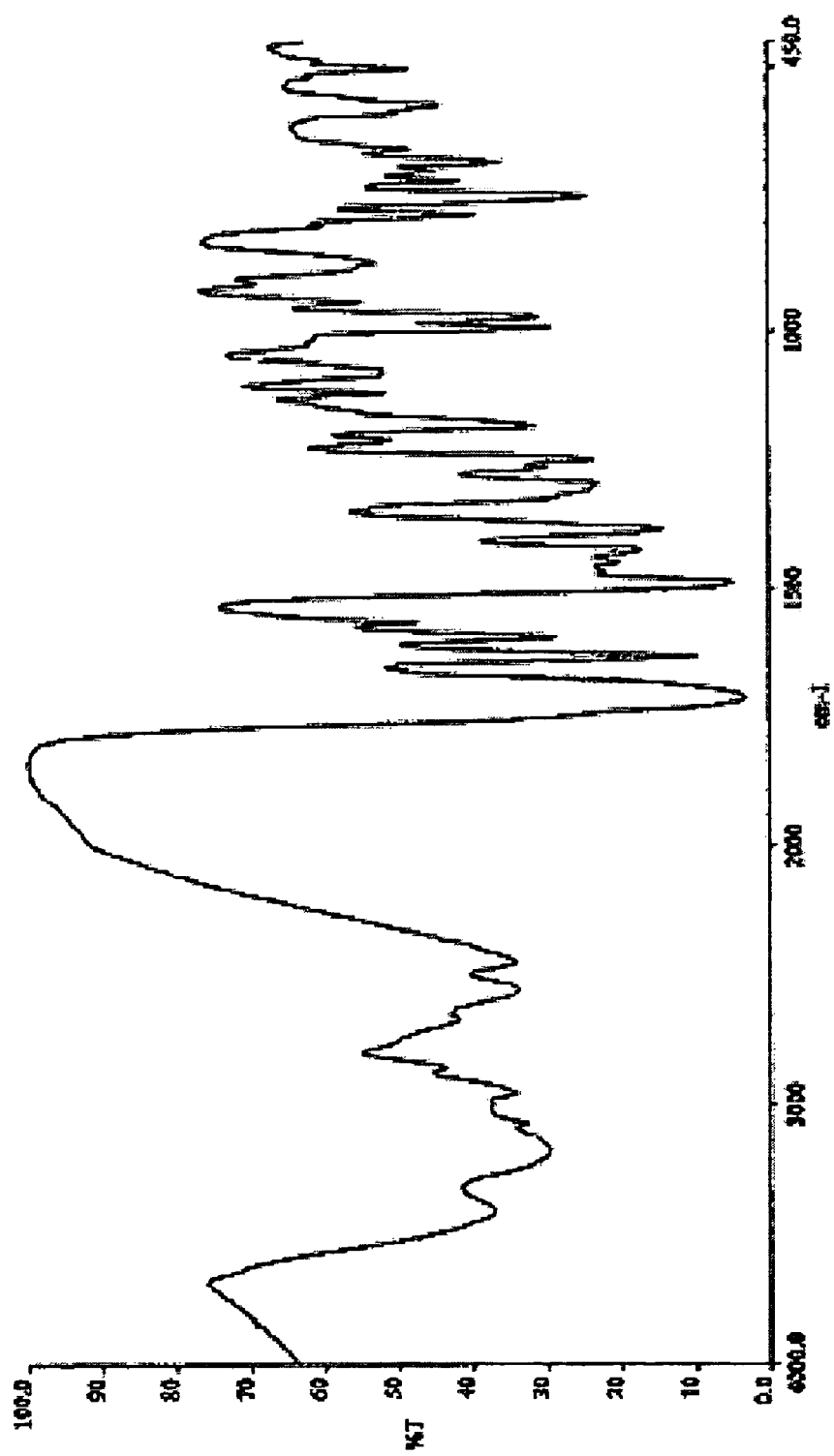
FIG. 2 is a typical example of an IR (KBr) Spectrum of a sample of Amorphous Ziprasidone Hydrochloride. Some of the peaks occur at about 3407.24; 3171.16; 2952.60; 2546.88; 2442.20; 1708.39; 1628.54; 1590.81; 1561.86; 1484.65; 1445.99; 1422.64; 1383.13; 1293.54; 1246.90; 1206.81; 1179.90; 1117.82; 1072.78; 992.41; 971.81; 943.16; 865.55; 774.23; 738.96; 701.98; 693.89; 677.49; 652.15; 568.58; and 500.07.
Figure 3:
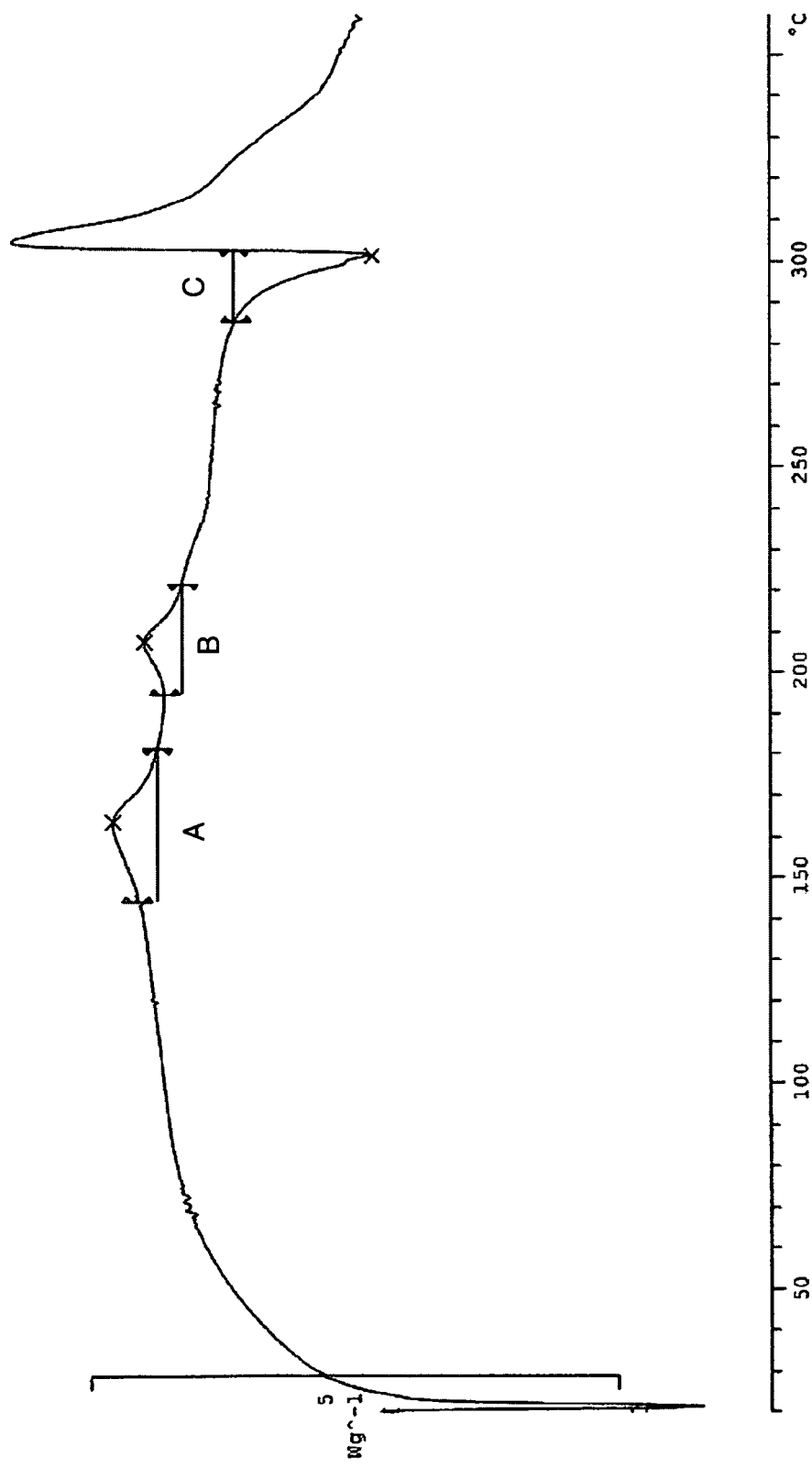
FIG. 3 is a typical DSC Thermogram of a sample of Amorphous Ziprasidone Hydrochloride. Method: 20.0-360.0° C. @ 10.00° C./min Al Std 40 µl N. Section A: Integral 60.31 mJ; normalized 54.44 $Jg^{-1}$; Onset 151.82° C.; Peak Height 0.43 $Wg^{-1}$; Extrapol. Peak 163.77° C.; Peak Width 22.63° C. Section B: Integral 35.83 ml; normalized 32.34 $Jg^{-1}$; Onset 201.79° C.; Peak Height 0.36 $Wg^{-1}$; Extrapol. Peak 207.09° C.; Peak Width 16.69° C. Section C: Integral −56.49 mJ; normalized −50.99 $Jg^{-1}$; Onset 293.12° C.; 1.30 $Wg^{-1}$; Extrapol. Peak 302.04° C.; Peak Width 5.73° C.

Preparation of amorphous 5-[2-[4-(1,2-benzisothiazol-3-yl)-1-piperazinyl]ethyl]-6-chloro-1,3-dihydro-2H-indol-2-one hydrochloride To a flask equipped with magnetic stirrer, thermometer and a gas bubbling tube was added 5-(2-(4-(1,2-benzisothiazol-3-yl)-1-piperazinyl)ethyl)-6-chloro-1,3-dihydro-2H-indol-2-one free base (5.0 g) and heptanes (100 mL) and the suspension was cooled to 0-5° C. under nitrogen. Anhydrous hydrogen chloride was bubbled into the suspension for 1-1.5 h. and then the suspension was stirred for about 2.5 h. The product was collected by filtration on a Buchner funnel. The filter cake is rinsed with heptanes at 20-25° C. and transferred to a drying oven and dried in vacuo at 55-60° C. for about 16 h. This afforded 5.38 g (98.9% yield) of amorphous ziprasidone hydrochloride. The, powder X-ray diffractogram, IR (KBr) spectrum and DSC thermogram are consistent with amorphous material. These are shown in FIGS. 1, 2 and 3 respectively.

Example 2

Preparation of amorphous 5-[2-[4-(1,2-benzisothiazol-3-yl)-1-piperazinyl]ethyl]-6-chloro-1,3-dihydro-2H-indol-2-one hydrochloride To a flask equipped with magnetic stirrer, thermometer and nitrogen inlet was added 5-(2-(4-(1,2-benzisothiazol-3-yl)-1-piperazinyl)ethyl)-6-chloro-1,3-dihydro-2H-indol-2-one free base (5.0 g) and dichloromethane (100 mL) and the suspension was stirred at 20-25° C. under nitrogen. A 20.5% anhydrous solution of hydrogen chloride in isopropanol (6.45 g) was added and the mixture was stirred for about 2 h. The product was collected by filtration on a Buchner funnel. The filter cake is rinsed with 3×10 mL of dichloromethane at 20-25° C. and transferred to a drying oven and dried in vacuo at 65-70° C. for about 18 h. The crude material was re-slurried at 20-25° C. for 10 minutes with heptanes and the suspension was filtered in vacuo. The filter cake is rinsed with heptanes at 20-25° C. and transferred to a drying oven and dried in vacuo at 65-70° C. for about 12 h. to afford amorphous ziprasidone hydrochloride having the same PXRD diffractogram, IR and DSC as shown in FIGS. 1 to 3.

Example 3

Preparation of amorphous 5-[2-[4-(1,2-benzisothiazol-3-yl)-1-piperazinyl]ethyl]-6-chloro-1,3-dihydro-2H-indol-2-one hydrochloride To a 1-L pressure reactor equipped with a mechanical stirrer and hydrogen chloride inlet and purge valve was added 5-(2-(4-(1,2-benzisothiazol-3-yl)-1-piperazinyl)ethyl)-6-chloro-1,3-dihydro-2H-indol-2-one free base (10.0 g) and heptanes (200 mL) and the suspension was cooled to about 0-5° C. and at about 150 rpm The vessel was pressurized to a hydrogen chloride pressure of 30 psi. After about 5 minute, the pressure had dropped to about 20 psi whereupon the pressure was increased to 30 psi. Over the next 10 minutes, the pressure had dropped to about 20 psi and then was stirred for 18 hours. The pressure was still at about 20 psi at which point the pressure was released and the vessel purged with nitrogen. The product was collected by filtration on a Buchner funnel. The filter cake is rinsed with 4×40 mL of heptanes and transferred to a drying oven and dried in vacuo at 65-70° C. for about 5 h to afford amorphous ziprasidone hydrochloride (9.22 g) having the same PXRD diffractogram, IR and DSC as shown in FIGS. 1 to 3.

While the foregoing provides a detailed description of the preferred embodiments of the invention, it is to be understood that the descriptions are illustrative only of the principles of the invention and not limiting. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A process for the preparation of an amorphous form of ziprasidone hydrochloride comprising:
    mixing ziprasidone free base with a first organic solvent selected from $C_5$ to $C_{12}$ substituted or unsubstituted cyclic and acyclic hydrocarbons and $C_1$ to $C_3$ chlorinated hydrocarbons to prepare a suspension;
    pressurizing a suitable pressure vessel with hydrogen chloride and the suspension, thereby forming a reaction mixture;
    stirring the reaction mixture to obtain ziprasidone hydrochloride formation; and
    isolating the amorphous ziprasidone hydrochloride.

2. The process of claim 1 wherein the first organic solvent is selected from hexanes, heptanes, cyclohexanes and mixtures thereof.

3. The process of claim 1 wherein the first organic solvent is selected from dichloromethane, chloroform and mixtures thereof.

4. The process of claim 1 wherein the first organic solvent is dichloromethane.

5. The process of claim 1 wherein the first organic solvent is heptanes.

6. The process according to claim 1 wherein the amount of the first organic solvent comprises about 5 to 100 volumes and the mixing and the pressurizing are carried out at a temperature of between about −10° C. to about 40° C.

7. The process according to claim 2 wherein the amount of the first organic solvent comprises about 5 to 100 volumes and the mixing and the pressurizing are carried out at a temperature of between about −10° C. to about 40° C.

8. The process according to claim 3 wherein the amount of the first organic solvent comprises about 5 to 100 volumes and the mixing and the pressurizing are carried out at a temperature of between about −10° C. to about 40° C.

9. The process according to claim 4 wherein the amount of the first organic solvent comprises about 5 to 100 volumes and the mixing and the pressurizing are carried out at a temperature of between about −10° C. to about 40° C.

10. The process according to claim 5 wherein the amount of the first organic solvent comprises about 5 to 100 volumes and the mixing and the pressurizing are carried out at a temperature of between about −10° C. to about 40° C.

11. The process of claim 1 wherein the amorphous form of ziprasidone hydrochloride is characterized by an x-ray powder diffraction pattern as shown in FIG. 1.

12. The process of claim 1 wherein the amorphous form of ziprasidone hydrochloride is characterized by an IR spectrum as shown in FIG. 2.

13. The process of claim 1 wherein the amorphous form of ziprasidone hydrochloride is characterized by a DSC thermogram as shown in FIG. 3.

14. The process of claim 1 further comprising drying the amorphous ziprasidone hydrochloride.

15. A process for the preparation of an amorphous form of ziprasidone hydrochloride comprising:
  mixing ziprasidone free base with a first organic solvent selected from $C_5$ to $C_{12}$ substituted or unsubstituted cyclic and acyclic hydrocarbons and $C_1$ to $C_3$ chlorinated hydrocarbons to prepare a suspension;
  pressurizing a pressure vessel with hydrogen chloride and the suspension, thereby forming a reaction mixture;
  stirring the reaction mixture to obtain ziprasidone hydrochloride formation;
  isolating the amorphous ziprasidone hydrochloride;
  stirring the amorphous ziprasidone hydrochloride with a second organic solvent selected from $C_5$ to $C_{12}$ substituted or unsubstituted cyclic and acyclic hydrocarbons and $C_1$ to $C_3$ chlorinated hydrocarbons, thereby forming a solution;
  filtering the solution thereby forming a filtrate; and
  drying the filtrate to obtain amorphous ziprasidone hydrochloride.

16. The process of claim 15 wherein the first organic solvent is selected from hexanes, heptanes, cyclohexanes and mixtures thereof.

17. The process of claim 15 wherein the first organic solvent is selected from dichloromethane, chloroform and mixtures thereof.

18. The process of claim 15 wherein the first organic solvent is dichloromethane.

19. The process of claim 15 wherein the first organic solvent is heptanes.

20. The process of claim 15 wherein the second organic solvent is selected from hexanes, heptanes, cyclohexanes and mixtures thereof.

21. The process of claim 15 wherein the second organic solvent is selected from dichloromethane, chloroform and mixtures thereof.

22. The process of claim 15 wherein the second organic solvent is dichloromethane.

23. The process of claim 15 wherein the second organic solvent is heptanes.

24. The process of claim 15 wherein the first solvent and the second solvent are the same.

25. The process of claim 15 wherein the amount of the first organic solvent comprises about 5 to 100 volumes and the mixing and the pressurizing are carried out at a temperature of between about −10° C. to about 40° C.

26. The process according to claim 16 wherein the amount of the first organic solvent comprises about 5 to 100 volumes and the mixing and the pressurizing are carried out at a temperature of between about −10° C. to about 40° C.

27. The process according to claim 17 wherein the amount of the first organic solvent comprises about 5 to 100 volumes and the mixing and the pressurizing are carried out at a temperature of between about −10° C. to about 40° C.

28. The process according to claim 18 wherein the amount of the first organic solvent comprises about 5 to 100 volumes and the mixing and the pressurizing are carried out at a temperature of between about −10° C. to about 40° C.

29. The process according to claim 19 wherein the amount of the first organic solvent comprises about 5 to 100 volumes and the mixing and the pressurizing are carried out at a temperature of between about −10° C. to about 40° C.

30. The process according to claim 20 wherein the amount of the first organic solvent comprises about 5 to 100 volumes and the mixing and the pressurizing are carried out at a temperature of between about −10° C. to about 40° C.

31. The process according to claim 24 wherein the amount of the first organic solvent comprises about 5 to 100 volumes and the mixing and the pressurizing are carried out at a temperature of between about −10° C. to about 40° C.

32. The process according to claim 22 wherein the amount of the first organic solvent comprises about 5 to 100 volumes and the mixing and the pressurizing are carried out at a temperature of between about −10° C. to about 40° C.

33. The process according to claim 23 wherein the amount of the first organic solvent comprises about 5 to 100 volumes and the mixing and the pressurizing are carried out at a temperature of between about −10° C. to about 40° C.

34. The process according to claim 24 wherein the amount of the first organic solvent comprises about 5 to 100 volumes and the mixing and the pressurizing are carried out at a temperature of between about −10° C. to about 40° C.

* * * * *